United States Patent [19]

Lewis

[11] Patent Number: 5,189,131

[45] Date of Patent: Feb. 23, 1993

[54] HYDROSILYLATION METHOD

[75] Inventor: Larry N. Lewis, Scotia, N.Y.

[73] Assignee: General Electric Company, Schenectady, N.Y.

[21] Appl. No.: 691,901

[22] Filed: Apr. 26, 1991

[51] Int. Cl.$^5$ ............................................. C08G 77/06
[52] U.S. Cl. ...................................... 528/15; 556/479
[58] Field of Search ........................... 556/479; 528/15

[56] References Cited

U.S. PATENT DOCUMENTS 5,025,073  6/1991  Lewis et al. ........................... 528/15
5,089,582  2/1992  Lewis .................................... 528/15

Primary Examiner—Melvyn I. Marquis
Attorney, Agent, or Firm—William A. Teoli; William H. Pittman

[57] ABSTRACT

The use of an effective amount of a cyclodextrin has been found to enhance the rate of addition between a silicon hydride and an olefinically unsaturated material in the presence of a platinum catalyst.

5 Claims, No Drawings

HYDROSILYLATION METHOD

BACKGROUND OF THE INVENTION

The present invention relates to a hydrosilylation method involving the platinum catalyzed addition of a silicon hydride and an olefinically unsaturated material in the presence of an effective amount of a cyclodextrin which enhances the rate of silicon hydride-olefin addition.

Prior to the present invention as shown by Schilling, U.S. Pat. No. 4,614,812, a hydrosilyl compound such as trichlorosilane can be effective as a promoter for hydrosilylation reactions.

Although the process of U.S. Pat. No. 4,614,812 has been found to provide an increase in the rate of forming silicon-carbon compounds, it can result in the formation of unwanted by-products derived from the use of the hydrosilylation promoter. Additional procedures are therefore constantly being evaluated for further enhancing the yields and reaction rates in methods of preparing desired organosilicon materials by a hydrosilylation mechanism.

SUMMARY OF THE INVENTION

The present invention is based on the discovery that a cyclodextrin can be used to greatly enhance the rate of platinum catalyzed hydrosilylation reactions. This result is quite surprising, since as shown in copending application Ser. No. 07/424,022, filed Oct. 19, 1989 now U.S. Pat. No. 5,025,073, cyclodextrin, such as $\beta$-cyclodextrin, has been found to be effective for converting a platinum catalyst to the latent state when employed in a hydrosilylation reaction as an inclusion compound of a complex of a platinum halide and a diene.

STATEMENT OF THE INVENTION

There is provided by the present invention a hydrosilylation method which comprises effecting reaction between a silicon hydride and an olefinically unsaturated material in the presence of an amount of a platinum catalyst which is sufficient to catalyze the addition between the silicon hydride and the olefinically unsaturated material and an amount of a cyclodextrin which is sufficient to enhance the rate of such addition.

Some of the olefinically unsaturated materials which can be used in the practice of the method of the present invention are organic materials such as, styrene, 1-hexene, 1-pentene, and 3,3'-dimethyl-1-butene.

In addition to organic materials, the olefinically unsaturated material which can be used in the practice of the method of the invention also can include silicon materials having olefinic unsaturation such as trimethyl vinyl silane, trichloro vinyl silane, and 1,1,3,3-tetramethyl-1,3-divinyl disiloxane.

Some of the silicon hydrides which can be used in the practice of the hydrosilylation method of the present invention are, for example, triethoxy silane, triethyl silane, trichloro silane, dimethylethoxy silane, and methyldiethoxy silane.

The cyclodextrins which can be used in the practice of the present invention are for example, $\alpha$, $\beta$, and $\gamma$-cyclodextrin as well as substituted cyclodextrins such as $\beta$-cyclodextrins with 7, 14 or 21 methyl substituents on the hydroxy groups.

An effective amount of cyclodextrin is 0.1 to 10 parts of cyclodextrin, per 100 parts by weight of hydrosilylation mixture. An effective amount of platinum catalyst is 5 ppm to 250 ppm of platinum based on the weight of hydrosilylation mixture.

Some of the platinum catalysts which can be used in the practice of the present invention to effect addition between silicon hydride and olefinically unsaturated materials are for example chloroplatinic acid, finely divided platinum metal, platinum metal on a carrier, such as carbon as shown by Daly, U.S. Pat. No. 2,970,150, platinum catalyst as shown by Ashby, U.S. Pat. Nos. 3,159,601 and 3,159,662, Lamoreaux, U.S. Pat. No. 3,220,972 and Karstedt, U.S. Pat. No. 3,775,452, all of which are incorporated herein by reference.

In order that those skilled in the art will be better able to practice the present invention, the following examples are given by way of illustration and not by way of limitation.

EXAMPLE 1

Equal molar amounts of triethoxysilane (5 mL) and styrene (3.1 mL) were combined with 10 microliters of a 5% platinum siloxane complex in xylene as shown by Karstedt, U.S. Pat. No. 3,775,452. After 30 minutes at 50° C. with stirring, there was obtained 45% yield of phenylethyltriethoxysilane based on gas chromatography analysis. The same reaction was repeated except that 0.25 g of $\beta$-cyclodextrin was added to the mixture. After 30 minutes at 50° C., there was obtained a 100% conversion to phenylethyltriethoxysilane based on gas chromatography analysis.

EXAMPLE 2

The procedure of example 1 was repeated, except that the reactions were run for 17 hours at ambient temperatures. The reaction run free of cyclodextrin showed a 50% conversion, whereas 100% conversion was achieved when 0.1 of the $\beta$-cyclodextrin was added to the mixture based on gas chromatography analysis.

EXAMPLE 3

The procedure of example 2 was repeated except that 0.1 g of a dimethylcyclodextrin ($\beta$-cyclodextrin with 14 methyl substituents on hydroxy groups) was used. It was found that a 70% conversion was realized after 17 hours of reaction based on gas chromatography analysis.

EXAMPLE 4

Equal molar amounts of triethoxysilane (5 mL, 26.7 mmol) and trimethylvinylsilane (3.9 mL, 26.9 mmol) were mixed with 10 microliters of the platinum catalyst of example 1. The mixture was stirred at ambient temperature. After 24 minutes, the mixture was colorless and gas chromatography analysis showed that a 60% addition had occurred between the triethoxysilane and the trimethylvinylsilane.

The same reaction was repeated except that 0.1 g of $\beta$-cyclodextrin was initially added to the mixture. It was found that after 12 minutes, the mixture underwent an exotherm and a change in color from colorless to brown. An analysis of the mixture showed 100% addition had occurred based on gas chromatography analysis.

EXAMPLE 5

The procedure of example 4 was repeated except that 10 microliters was used of a 3.8% platinum catalyst in the form of a reaction product of $H_2PtCl_6$ and octanol shown by Lamoreaux, U.S. Pat. No. 3,197,432. When a mixture free of $\beta$-cyclodextrin was used, no reaction resulted after several hours. However, a mixture containing 0.1 g of $\beta$-cyclodextrin showed a vigorous exotherm after 10 minutes and 100% conversion to 1,2-triethoxysilyl, trimethylsilylethane based on gas chromatography analysis.

EXAMPLE 6

Equal molar amounts of triethylsilane (5 mL, 31.4 mmol) and trimethylvinylsilane (4.6 mL, 31.7 mmol) were mixed with 10 microliters of the platinum catalyst of example 1. The mixture was stirred at ambient temperature. After 3 hours, $^1H$ NMR analysis showed that 59% of conversion to products had occurred. The same procedure was repeated except that 0.1 g of $\beta$-cyclodextrin was added. After 3 hours of reaction there was obtained a 71% conversion to products based on gas chromatography analysis.

Although the above examples are directed to only a few of the very many variables which can be used in the practice of the method of the present invention, it should be understood that the present invention is directed to the use of a much broader variety of silicon hydrides and olefinically unsaturated materials as well as platinum catalyst and cyclodextrin as shown in the description preceding these examples.

What is claimed is:

1. A method for enhancing the rate of addition between a silicon hydride and an olefinically unsaturated material in a platinum catalyzed hydrosilylation reaction, which comprises adding to a hydrosilylation mixture, 0.1 to 10 parts by weight of cyclodextrin, per 100 parts by weight of the hydrosilylation mixture.

2. A method in accordance with claim 1, where the cyclodextrin is $\beta$-cyclodextrin.

3. A method in accordance with claim 1, where the platinum catalyst is a platinum siloxane complex.

4. A method in accordance with claim 1, where the platinum catalyst is a reaction product of $H_2PtCl_6$ in octanol.

5. A method in accordance with claim 1, where the silicon hydride is triethoxysilane and the olefinically unsaturated material is styrene.

* * * * *